(12) United States Patent
Schroeder et al.

(10) Patent No.: US 7,331,354 B2
(45) Date of Patent: Feb. 19, 2008

(54) CLEANING OF TRAY COLUMNS WHICH HAVE BEEN USED FOR RECTIFICATIVELY TREATING LIQUIDS COMPRISING (METH)ACRYLIC ACID AND/OR ESTERS THEREOF

(75) Inventors: Juergen Schroeder, Ludwigshafen (DE); Klaus Joachim Mueller-Engel, Stutensee (DE); Volker Schliephake, Schifferstadt (DE); Ulrich Hammon, Mannheim (DE); Volker Diehl, Ellerstadt (DE); Ulrich Jaeger, Roemerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/505,163

(22) PCT Filed: Mar. 4, 2003

(86) PCT No.: PCT/EP03/02186

§ 371 (c)(1),
(2), (4) Date: Aug. 30, 2004

(87) PCT Pub. No.: WO03/076385

PCT Pub. Date: Sep. 18, 2003

(65) Prior Publication Data

US 2005/0115590 A1    Jun. 2, 2005

(30) Foreign Application Priority Data

Mar. 13, 2002   (DE) ................................ 102 11 273

(51) Int. Cl.
*B08B 3/00* (2006.01)
*B08B 9/00* (2006.01)
*B08B 9/027* (2006.01)
*B08B 3/08* (2006.01)

(52) U.S. Cl. ............... 134/22.18; 134/22.1; 134/22.11; 134/22.12; 134/22.13; 134/22.17; 134/29; 134/30; 134/36; 134/37

(58) Field of Classification Search ............... 134/22.1, 134/22.11, 22.12, 22.13, 22.17, 22.18, 29, 134/30, 36, 37
See application file for complete search history.

(56) References Cited

U.S. PATENT DOCUMENTS

| 3,958,964 | A | * | 5/1976 | Koch | .......................... 96/181 |
| 3,969,094 | A | * | 7/1976 | Dunson et al. | ................. 96/228 |
| 2004/0026228 | A1 | * | 2/2004 | Diehl et al. | .................... 203/96 |

FOREIGN PATENT DOCUMENTS

| DE | 195 36 179 | 4/1997 |
| DE | 197 46 688 | 4/1999 |
| EP | 1 033 359 | 9/2000 |
| WO | 01/51159 | 7/2001 |

OTHER PUBLICATIONS

Kirk Othmer, Encyclopedia of Chemical Technology, 4th edition, vol. 1 pp. 301-302.

* cited by examiner

*Primary Examiner*—Zeinab El-Arini
(74) *Attorney, Agent, or Firm*—Oblon, Spivak, McClelland, Maier & Neustadt, P.C.

(57) ABSTRACT

In process for cleaning tray columns which are used for the purposes of rectifiying liquids comprising (meth)acrylic compounds, a basic liquid is conveyed downward through the tray column and a gas is passed through the column in countercurrent to the basic liquid at an average gas phase differential pressure over all trays of at least 0.5 mbar/tray.

11 Claims, No Drawings

CLEANING OF TRAY COLUMNS WHICH HAVE BEEN USED FOR RECTIFICATIVELY TREATING LIQUIDS COMPRISING (METH)ACRYLIC ACID AND/OR ESTERS THEREOF

The present invention relates to a process for cleaning tray columns which have been used for rectificatively treating liquids comprising (meth)acrylic acid and/or esters thereof by conveying a basic liquid downward through the tray column.

In this document, (meth)acrylic acid is an abbreviated notation for acrylic acid or methacrylic acid. These and their esters are valuable starting compounds for preparing polymers obtainable by free radical polymerization which find use, for example, as adhesives.

(Meth)acrylic acid itself is industrially prepared principally by. heterogeneously catalyzed gas phase oxidation of the appropriate alkenes, alkanes or the corresponding $\alpha,\beta$-ethylenically unsaturated aldehydes. However, this does not form pure (meth)acrylic acid. Rather, a product mixture is formed from which the (meth)acrylic acid has to be removed. To this end, the (meth)acrylic acid is customarily absorbed in a solvent and subsequently removed via various rectification stages, optionally with the addition of azeotroping agents, from absorbents and secondary components absorbed in addition to (meth)acrylic acid and contained therein. Alternatively, the product gas mixture may also be fractionally condensed and the (meth)acrylic acid-condensates obtained may be worked up rectificatively.

Esters of (meth)acrylic acid are generally prepared on the industrial scale by direct esterification of (meth)acrylic acid with alcohols, for example alkanols, in the presence of strong acids and optionally of an azeotroping agent to remove water of esterification, or by transesterification of (meth)acrylic esters with suitable alcohols, for example alkanols. The target ester is likewise customarily removed from the product mixture predominantly rectificatively (cf., for example, EP-A 10 33 359, DE-A 19 746 688, DE-A 19 536 179 and Kirk Othmer, Encyclopedia of Chemical Technology, 4th ed., Vol. 1, pages 301-302).

Both in the case of the abovementioned rectificative removal of (meth)acrylic acid and also its esters, the rectification columns used are generally tray columns, i.e. columns which have trays as their internals.

The trays of a tray column are permeable toward both the vapor rising in the tray column and also the liquid phase refluxing in the tray column. Between the rising vapor and refluxing liquid phase, in particular on the trays, there is heat and mass transfer as a consequence of the disturbed equilibrium, which ultimately results in the separation desired in the column.

A disadvantage of the rectificative removal of (meth) acrylic acid and/or its esters is that on the one hand the rectification is a thermal separating process and on the other hand the (meth)acrylic compounds are compounds having high boiling points and at the same time a marked tendency to free radical polymerization, in particular under the action of heat. Typical rectification temperatures are generally above 100° C. This also applies to rectifications under reduced pressure.

The (meth)acrylic compounds are accordingly subjected in rectifications to temperature stresses which can easily set off an undesired polymerization. The formation of undesired polymer fouling which in extreme cases is able to block the tray column and make it impermeable is generally the consequence. Although efforts are made in practice to prevent the undesired free radical polymerization by the addition of suitable polymerization inhibitors, this does not allow complete elimination of polymer formation to be achieved. In other words, the tray column generally has to be freed of polymer, i.e. cleaned, after a few weeks.

DE-A 19 746 688, DE-A 19 536 179 and EP-A 10 33 359 disclose a process for cleaning tray columns which have been used for rectificatively treating liquids comprising (meth)acrylic acid and/or esters thereof by conveying a basic liquid downward through the tray column.

However, a disadvantage of this procedure is that the cleaning rate obtained is not completely satisfactory.

It is an object of the present invention to provide an improved cleaning process.

We have found that this object is achieved by a process for cleaning tray columns which have been used for rectificatively treating liquids comprising (meth)acrylic acid and/or esters thereof by conveying a basic liquid downward through the tray column, which comprises passing a gas through the tray column in countercurrent to the basic liquid in such a manner that, during the cleaning, the difference between the pressure in the gas phase immediately below the lowermost tray of the tray column and the pressure in the gas phase immediately above the uppermost tray of the tray column divided by the number of trays in the column is at least 0.5, frequently from 0.5 to 6, mbar per tray.

Preference is given to passing the gas through the tray column at such a rate that the abovementioned average pressure drop between two successive trays is from 1 to 5 mbar and more preferably from 2 to 4 mbar.

The trays in the tray column may be, for example, dual-flow trays, sieve trays, valve trays, Thormann trays, tunnel cap trays and/or bubble cap trays.

The gas to be passed through the tray column in the process according to the invention may substantially be any gas. Preference is given to using nitrogen, air, air diluted with nitrogen and/or steam.

To convey the gas, compressors and/or vacuum pumps may be used.

The basic liquids used for the process according to the invention may be all those recommended by DE-A 19 746 688, DE-A 19 536 179 and EP-A 10 33 359.

These are in particular aqueous alkali metal and/or alkaline earth metal hydroxide and/or oxide solutions, in particular the aqueous solutions of NaOH, KOH and $Ca(OH)_2$. In general, the aqueous solution has a dissolved salt content of from 0.01 to 30% by weight, preferably from 0.5 to 10% by weight.

In an advantageous development of the invention, a substantially pH-neutral (based on its aqueous solution) alkali metal and/or alkaline earth metal salt is added to the abovementioned basic aqueous alkali metal solution in a ratio of >0:1 to 2:1 (weight ratio of neutral salt to hydroxide and/or oxide). For this purpose, the sulfates, acetates, oxalates, carbonates, hydrogensulfates, hydrogencarbonates and/or other salts corresponding to the hydroxidic/oxidic compounds are particularly suitable. Such an addition allows the dissolution behavior of the basic solution for the process according to the invention to be further improved.

According to the invention, basic polar organic solvents such as amines or amides, preferably acetamides, more preferably monoacetamide ($CH_3CONH_2$) may also be used as the basic liquid instead of basic aqueous solutions. Further basic liquids which may be used according to the invention include monomethylacetamide ($CH_3CON(CH_3)$H), dimethylacetamide ($CH_3CON(CH_3)_2$) and dimethylformamide ($HCON(CH_3)_2$).

The temperatures at which the flushing according to the invention is carried out are substantially determined by the boiling point of the basic liquid used, since the dissolution behavior of all of the basic liquids mentioned increases with increasing temperature. The optimum use temperature for the aqueous alkali metal and/or alkaline earth metal hydroxide solutions is from >80° C. to about 115° C. at atmospheric pressure, preferably from 90° C. to 110° C. For the amides described, the optimum use temperature in each case is from 10 to 1° C. below the boiling point of these substances. When the vapor phase of the basic flushing liquid itself is used as the gas passed in countercurrent through the tray column (for example steam), the use temperature is regularly the boiling point.

The process according to the invention may either be carried out at regular intervals or else after detecting a certain degree of polymer formation.

The liquids comprising (meth)acrylic acid and/or esters thereof which have been rectificatively treated beforehand in the tray column to be cleaned according to the invention may comprise $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight of (meth)acrylic acid and/or esters thereof. The esters may be the esters of monohydroxy- and/or polyhydroxy alcohols.

In particular, the (meth)acrylic esters comprise the esters of (meth)acrylic acid with alkanols ($C_1$— to $C_{12}$—, preferably $C_1$— to C8—) and/or alkanediols. These are in particular methyl acrylate, methyl methacrylate, ethyl acrylate, ethyl methacrylate, n-butyl acrylate, tert-butyl acrylate, tert-butyl methacrylate and also 2-ethylhexyl acrylate, but also the esters of dimethylaminoethanol.

Examples of polymerization inhibitors added for very substantial suppression of polymer formation during rectification include stabilizers such as phenothiazine, hydroquinone monomethyl ether and hydroquinone.

The advantage of the process according to the invention is that the polymer removal only entails small time demands. The final result is thus to allow a short interruption time of the rectification process and also complete removal of the polymer deposits.

Before the process according to the invention and after carrying out the process according to the invention, the tray column is flushed with water in a manner known to those skilled in the art. It is advantageous to convey a gas through the tray column in countercurrent to the flushing water in a similar manner to the process according to the invention.

Finally, the tray column is dried and operated further.

Polymer fouling generally shows itself in the process according to the invention by an increasing pressure drop when operating the tray column.

So that tray columns are easy to clean by the process according to the invention, they are advantageously equipped with a flushing line. This facilitates the transport to the top of the column of the basic flushing liquid which is heated, for example, in the evaporator of the column. Customarily, the flushing liquid is added via the reflux line of the rectification column.

The process according to the invention may be carried out at atmospheric pressure, elevated pressure or at reduced pressure. In this document, the pressure in the gas phase "immediately" below the lowermost or above the uppermost tray of the tray column means that the measuring point should not be more than 15 cm below the lowermost and at least 25 cm above the uppermost tray. The pressure measurement may be effected, for example, via an open drillhole, in which a pressure transducer is connected to the column via a wall nozzle.

It will be appreciated that the procedure according to the invention may also be applied to columns which have internals other than trays (for example Raschig rings, Pall rings or structure packings) and in which liquids comprising (meth)acrylic compounds have been rectified and/or in which the vapours comprising (meth)acrylic monomers have been absorbed.

It is also applicable when the column in question has become fouled with polymer in the course of an absorption of (meth)acrylic compounds from the gas phase.

Overall, the advantageousness of the process according to the invention is based on the flushing liquid passed downward through the column under the given boundary conditions forming liquid whirlpools, in particular on the column trays, which effect the accelerated cleaning.

EXAMPLE

In a tray column (material: a stainless steel having the materials number 1.4571 according to DIN standard EN 10020) of diameter 3.8 m and length 32 m, acrylic acid was rectificatively removed via the feed line of the column from the liquid composed as described below (feed rate=114 metric tons/h).

The liquid comprised:

| | |
|---|---|
| 17% by weight of | acrylic acid, |
| 0.02% by weight of | water, |
| 0.0015% by weight of | acrolein, |
| 0.0015% by weight of | acryl acrylate, |
| 0.01% by weight of | furfural, |
| 0.027% by weight of | acetic acid, |
| 0.2% by weight of | benzaldehyde, |
| 0.003% by weight of | propionic acid, |
| 0.032% by weight of | maleic anhydride, |
| 58% by weight of | diphyl, |
| 17.0% by weight of | dimethyl phthalate, |
| 3% by weight of | acryloylpropionic acid and |
| 0.02% by weight of | phenothiazine. |

The tray column comprised 45 dual-flow trays (material: a stainless steel having the materials number 1.4571 according to DIN standard EN 10020). 37 trays were above the feed point and 8 trays were below the feed point of the acrylic acid-containing liquid. The dual-flow trays above the feed had drillholes of diameter 25 mm and the dual-flow trays below the feed had drillholes of diameter 50 mm (each measured internally). The acrylic acid-containing liquid was separated into 99.6% by weight acrylic acid, a mixture of components having lower boiling points than acrylic acid and a mixture of components having higher boiling points than acrylic acid which comprised less than 0.5% by weight of acrylic acid. The homogeneous separation of the dual-flow trays over the entire tray column was 400 mm. The temperature at the top of the column was 80° C., the pressure at the top of the column 105 mbar and the reflux ratio (ml of reflux liquid to ml of liquid withdrawal) was 1.3. The temperature at the bottom of the column was 193° C. and the pressure at the bottom of the column 230 mbar. The reflux of the column was stabilized with phenothiazine in such a manner that 99.6% by weight acrylic acid withdrawn via the sidestream takeoff (on tray 35, counted from below) comprised 250 ppm by weight of PTZ. The PTZ was added dissolved in acrylic acid removed in this manner (1.5% by weight solution).

After a running time of 21 days, the rectification column was shut down, emptied and then flushed for two hours with water of temperature 30° C. The flushing water was fed to the tray column via its upper reflux line in free fall and circulated by pumping via the same (300 m3/1). The used flushing water was withdrawn from the column after the end of the flushing. The diphyl/dimethyl phthalate mixture contained therein could be recovered by steam distillation.

The tray column was then inspected.

In the region below the sidestream takeoff (in particular in the region of from tray 30 to tray 35), there were about 250 kg of polymer. The polymer adhered both to the trays (about 60%) and also to the tray undersides (about 40%).

Flushing was then effected using a 5% by weight aqueous sodium hydroxide solution. The aqueous sodium hydroxide solution was fed to the tray column via the feed line in free fall and circulated by pumping via the same (300 m$^3$/h). The liquid phase evaporator of the tray column was switched on in order to set the temperature of the sodium hydroxide solution to from 90 to 95° C.

After one hour, the feed (in free fall) was switched to the upper reflux line and the sodium hydroxide solution circulated by pumping for a further six hours via the same (300 m$^3$/h). Over the entire duration of the sodium hydroxide solution flushing, 600 m$^3$/h of air at ambient temperature was fed to the column below the first tray. The average gas phase differential pressure over all trays was 2 mbar/tray. After the end of the flushing, the used flushing solution was withdrawn from the tray column. The diphyl/dimethyl phthalate mixture contained therein could be recovered by steam distillation. The tray column was then inspected. The polymer had been removed apart from small residues (<5 kg).

COMPARATIVE EXAMPLE

The procedure of the example was repeated. After the water flushing, the rectification column was inspected. In the region below the sidestream takeoff, there were about 200 kg of polymer. The polymer adhered both to the trays (about 50%) and also to the tray undersides (about 50%).

Flushing with sodium hydroxide solution was then effected as in the example, except that there was no air feed. The average gas phase differential pressure over all trays was <<0.5 mbar/tray. After the end of the sodium hydroxide solution flushing, the rectification column was inspected. In the region below the sidestream takeoff, there were still about 80 kg of polymer. The polymer was both on the trays (about 40%) and also on the tray undersides (about 60%).

The sodium hydroxide solution flushing of the example, i.e. with air feed, was then repeated. The average gas phase differential pressure over all trays was 2.2 mbar/tray. After the second sodium hydroxide solution flushing, the tray column was inspected again. The polymer had been removed apart from small residues (<5 kg).

The pressure measurement in both the example and the comparative example was effected 10 cm below the lowermost or 30 cm above the uppermost tray via an open drillhole (separation from the upper edge of the drillhole), and a pressure transducer was connected to the column via a wall nozzle.

We claim:

1. A process for cleaning tray columns which have been used for rectificatively treating liquids comprising (meth) acrylic acid, esters of (meth)acrylic acid or mixtures of (meth)acrylic acid and esters of (meth)acrylic acid the process comprising
   conveying a basic liquid downward through the tray column, and
   passing a gas through the tray column in countercurrent to the basic liquid,
   wherein during the cleaning, a difference between a pressure in the gas immediately below a lowermost tray of the tray column and a pressure in the gas immediately above an uppermost tray of the tray column divided by the number of trays in the column is from 0.5 to 5 mbar per tray.

2. The process as claimed in claim 1, wherein, during the cleaning, the difference between the pressure in the gas phase immediately above the uppermost tray of the tray column and the pressure in the gas phase immediately below the lowermost tray of the tray column divided by the number of trays in the column is from 1 to 5 mbar per tray.

3. The process as claimed in claim 1, wherein, during the cleaning, the difference between the pressure in the gas phase immediately above the uppermost tray of the tray column and the pressure in the gas phase immediately below the lowermost tray of the tray column divided by the number of trays in the column is from 2 to 4 mbar per tray.

4. The process as claimed in claim 1, wherein the basic liquid is an aqueous solution of sodium hydroxide.

5. The process as claimed in claim 1, wherein the gas passed through the tray column in countercurrent to the basic liquid is air.

6. The process as claimed in claim 1, wherein the gas passed through the tray column in countercurrent to the basic liquid is selected from the group consisting of nitrogen, air, air diluted with nitrogen, steam and mixtures thereof.

7. The process as claimed in claim 6, wherein a material selected from the group consisting of a substantially pH-neutral alkali metal salt, an alkaline earth metal salt, and a mixture thereof, is added to the basic liquid.

8. The process as claimed in claim 6, wherein the basic liquid is utilized at a temperature of from >80° C. to about 115° C.

9. The process as claimed in claim 1, wherein the basic liquid is an aqueous solution of at least one selected from the group consisting of alkali metal hydroxide, alkaline earth metal hydroxide, NaOH, KOH and Ca(OH)$_2$.

10. The process as claimed in claim 1, wherein the basic liquid is a basic polar organic solvent.

11. The process as claimed in claim 10, wherein the basic polar organic solvent is an amine, amide or a mixture of amine and amide.

* * * * *